(12) United States Patent
Mackal

(10) Patent No.: US 8,308,128 B2
(45) Date of Patent: Nov. 13, 2012

(54) LEAF CLAMP FOR TUBING

(75) Inventor: Glenn H. Mackal, South Pasadena, FL (US)

(73) Assignee: Halkey-Roberts Corporation

( * ) Notice: Subject to any disclaimer, the term of this patent is extended or adjusted under 35 U.S.C. 154(b) by 1149 days.

(21) Appl. No.: 12/124,645

(22) Filed: May 21, 2008

(65) Prior Publication Data
US 2008/0290303 A1 Nov. 27, 2008

Related U.S. Application Data

(60) Provisional application No. 60/939,363, filed on May 21, 2007.

(51) Int. Cl.
*F16K 7/04* (2006.01)
(52) U.S. Cl. .............. 251/9; 251/10; 604/250
(58) Field of Classification Search ............. 251/4, 9, 251/10; 604/250
See application file for complete search history.

(56) References Cited

U.S. PATENT DOCUMENTS

| | | | |
|---|---|---|---|
| 4,697,785 A * | 10/1987 | Tuseth | 251/9 |
| 4,802,650 A * | 2/1989 | Stricker | 251/10 |
| 6,196,519 B1 * | 3/2001 | Utterberg | 251/10 |
| 6,427,874 B2 | 8/2002 | Brown | |
| 6,561,481 B1 | 5/2003 | Filonczuk | |
| 6,681,798 B2 | 1/2004 | Bueser | |
| 7,140,509 B2 * | 11/2006 | Yang | 251/9 |
| 7,686,279 B2 * | 3/2010 | Nerbonne et al. | 604/250 |

FOREIGN PATENT DOCUMENTS

WO 2008/064354 9/2008

OTHER PUBLICATIONS

PCT Rpt. on Patentability, May 21, 2008, Halkey-Roberts Corp.

* cited by examiner

*Primary Examiner* — Steven J Ganey
(74) *Attorney, Agent, or Firm* — Gray Robinson, P.A.

(57) ABSTRACT

A leaf clamp for installation on tubing to control the flow of fluid therethrough, the leaf clamp comprising opposing rectilinear frameworks between which the tubing is threaded. A flexible leaf interconnects the opposing frameworks and extends generally parallel above the tubing positioned between the rectilinear frameworks. A snap-lever, generally L-shaped, is pivotally connected between the upper portions of the frameworks such that the shorter leg of the L-shaped lever is aligned with and engages the leaf member to urge it downwardly into engagement with the tubing as the longer leg of the L-shaped snap-lever is pivoted from a generally transverse "open" position to a generally parallel "closed" position.

16 Claims, 5 Drawing Sheets

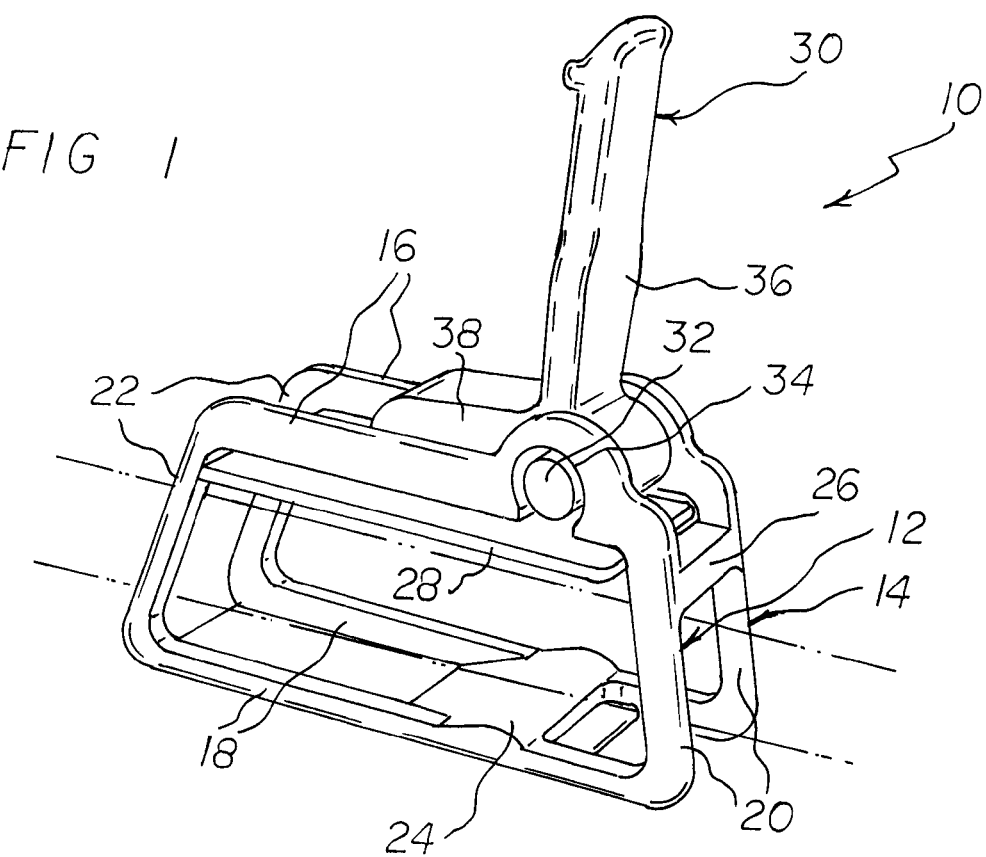
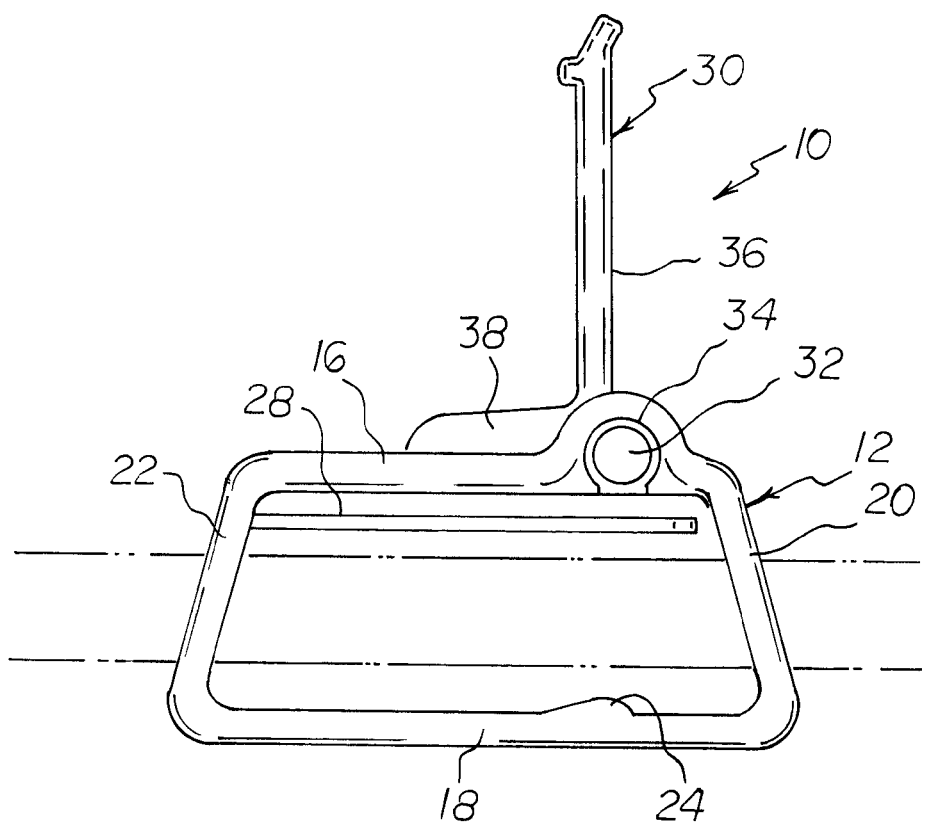

LEAF CLAMP FOR TUBING

CROSS-REFERENCE TO RELATED APPLICATIONS

This application claims the benefit of provisional patent application 60/939,363, filed May 21, 2007, the disclosure of which is hereby incorporated by reference herein.

BACKGROUND OF THE INVENTION

1. Field of the Invention

This invention relates to a clamp for hoses or flexible tubing. More particularly, this invention relates to hose clamps commonly used in the medical industry.

2. Description of the Background Art

Presently, there exist many types of clamps for clamping onto a hose or other flexible member to at least partially oculate the hose or to tightly close-off the hose. One particular industry that requires the use of hose clamps is the medical industry wherein hose clamps are used widely as tubing clamps in intravenous administration sets, catheterization kits, and many other medical assemblies.

One of the most common type of tubing clamp in the medical industry comprises a clam-shall design having upper and lower body members joined together by a living hinge. The medical tubing is positioned between the upper and lower body members which are allowed to clamp onto the tubing by means of the living hinge. Typically, the upper body member includes a pointed end that engages into teeth formed in the end of the lower body member to achieve a complementary ratchet mechanism such that the upper and lower body portions may be clamped onto the medical tubing to oculate fluid flow or to entirely close off all fluid flow. Further, the most widely used tubing clamp comprises a longitudinal hole formed through the living spring and the ratcheting portions of the lower body members such that the tubing is threaded therethrough in alignment with mating clamping elements.

Importantly, the inherent memory of the medical tubing is intended to be sufficient to fully separate the body members and open the valve once the ratchet mechanism is released so that fluid may fully flow through the tubing. Unfortunately, however, after the clamp has been clamped on the tubing for any significant period of time, it retains a "deflection set" which resists the force exerted by the tubing to return to its fully-opened position without oculation of the medical tubing. Furthermore, the deflection set visually obscures whether the clamp has been fully closed to close the tubing or whether the clamp is only partially closed allowing some fluid to flow through the tubing.

The entirety of the tubing clamp is typically manufactured as a one-piece injection-molded assembly. Therefore, the material constituting the body members and the hinge is the same. Selection of such material therefore requires conflicting characteristics; namely, for the ratchet mechanism a hard material is desired to assure proper latching whereas for the living spring, a more resilient material is desired to assure less of a deflection set characteristic.

Representative patents disclosing tubing clamps include U.S. Pat. Nos. 4,453,295; 4,588,160; 4,589,626; 4,643,389; Des. 427,307; Des. 431,650; and U.S. Pat. No. 6,592,558, the disclosures of each of which are hereby incorporated by reference herein.

Therefore, it is an object of this invention to provide an improvement which overcomes the aforementioned inadequacies of the prior art devices and provides an improvement which is a significant contribution to the advancement of the tubing clamp art.

Another object of this invention is to provide a tubing clamp comprising a leaf member that is forced into engagement with the tubing by a snap-lever when the snap-lever is closed to fully close-off all fluid flow within the tubing.

Another object of this invention is to provide a tubing clamp comprising a pivotable snap-lever component that actuates against a housed leaf component to fully close off fluid flow within the tubing, wherein the components of the tubing clamp may be injection-molded fully assembled together even though they are rotatably articulatable with respect to each other.

The foregoing has outlined some of the pertinent objects of the invention. These objects should be construed to be merely illustrative of some of the more prominent features and applications of the intended invention. Many other beneficial results can be attained by applying the disclosed invention in a different manner or modifying the invention within the scope of the disclosure. Accordingly, other objects and a fuller understanding of the invention may be had by referring to the summary of the invention and the detailed description of the preferred embodiment in addition to the scope of the invention defined by the claims taken in conjunction with the accompanying drawings.

SUMMARY OF THE INVENTION

For the purpose of summarizing this invention, the invention comprises a leaf clamp for installation on tubing to control the flow of fluid therethrough. The leaf clamp comprises opposing rectilinear frameworks between which the tubing is threaded. A flexible leaf interconnects the opposing frameworks and extends generally parallel above the tubing positioned between the rectilinear frameworks. A snap-lever, generally L-shaped, is pivotally connected between the upper portions of the frameworks such that the shorter leg of the L-shaped lever is aligned with and engages the leaf member to urge it downwardly into engagement with the tubing as the longer leg of the L-shaped snap-lever is pivoted from a generally transverse "open" position to a generally parallel "closed" position.

Notably, the angle between the legs of the generally L-shaped snap-lever is preferably obtuse such that upon movement of the snap-lever to its parallel "closed" position, the resilient force of the tubing being squeezed by the leaf member snaps the snap-lever fully closed. Conversely, movement of the longer leg of the L-shaped member from its parallel "closed" position to a generally transverse position causes the snap-lever to snap open.

The generally L-shaped snap-lever and the opposing rectilinear frameworks joined by the leaf member may be injection molded as separate components and then subsequently assembled. Alternatively, they may be injection molded fully assembled in accordance with my corresponding application entitled "Apparatus and Method for Injection Molding a Fully-Assembled Multi-Component Articulatable Device", Ser. No. 60/939,347, filed May 21, 2007 and Ser. No. 12/124, 342, filed May 21, 2008, the disclosures of which are hereby incorporated by reference herein.

Importantly, unlike prior art clam-shell tube clamps, the leaf clamp of the present invention does not depend upon the memory of the clamp to open properly. Rather, the L-shaped snap-lever whose shorter leg engages the leaf member assures that the snap-lever will remain fully open once its longer leg is moved from the generally parallel "closed" position to a generally transverse "open" position. Greater tactile indication of opening as well as closure is attained. Further, unlike prior art clam-shell tubing clamps, the snapping action of the leaf clamp of the present invention can be operated one-handedly, to either close or open the clamp onto the tubing. Finally, the use of the leaf member onto which the shorter leg of the L-shaped snap-lever engages, significantly reduces tubing wear and abrasion that would otherwise occur with a sliding/closing action directly onto the tubing.

The foregoing has outlined rather broadly the more pertinent and important features of the present invention in order that the detailed description of the invention that follows may be better understood so that the present contribution to the art can be more fully appreciated. Additional features of the invention will be described hereinafter which form the subject of the claims of the invention. It should be appreciated by those skilled in the art that the conception and the specific embodiment disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims.

BRIEF DESCRIPTION OF THE DRAWINGS

For a fuller understanding of the nature and objects of the invention, reference should be had to the following detailed description taken in connection with the accompanying drawings in which:

FIG. 1 is a perspective view of the leaf clamp of the invention showing in phantom a length of tubing threaded between its rectilinear opposing frameworks;

FIG. 2 is a side view of FIG. 1 showing the leaf member interconnecting the opposing rectilinear frameworks at its rear end and free floating on its other end proximate to the front of the snap-lever and showing in phantom a length of tubing threaded between its rectilinear opposing frameworks;

Similar reference characters refer to similar parts throughout the several views of the drawings.

DETAILED DESCRIPTION OF THE PREFERRED EMBODIMENT

Figure 3:
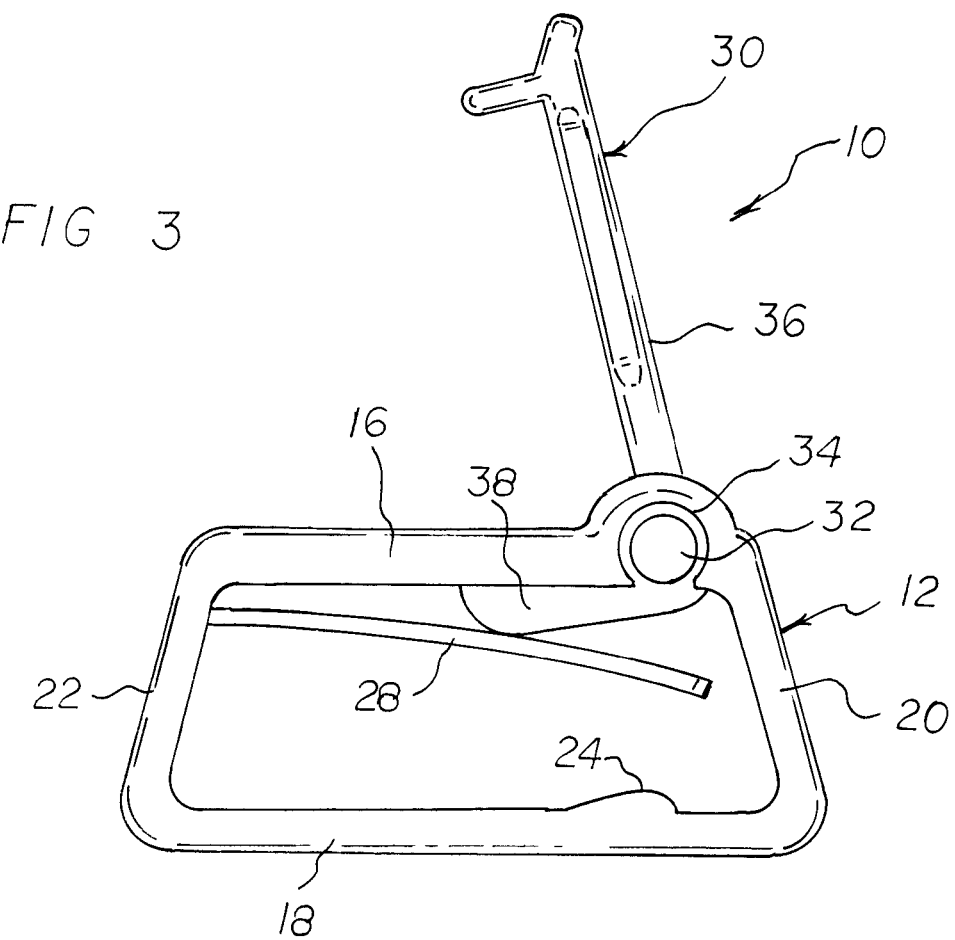
FIG. 3 is a side elevational view similar to that of FIG. 2 in a partially-closed position immediately prior to being snapped fully closed due to the obtuse angle between the longer and shorter legs of the snap-lever.
Figure 4:
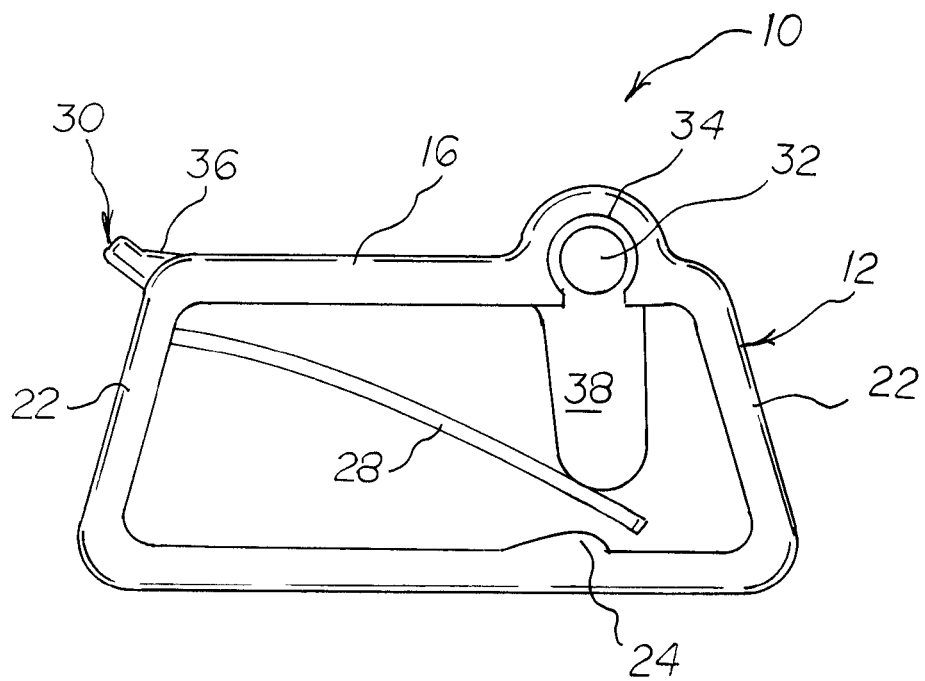
FIG. 4 is a side view similar to that of FIG. 3 but immediately after full closure whereupon the angle of the shorter leg of the snap-lever moves beyond normal whereupon the inherent resiliency of the tubing exerts a force upwardly to competently snap the snap-lever closed in its parallel position.

Referring to FIGS. 1-6, the leaf clamp 10 of the invention comprises a pair of opposing rectilinear frameworks 12 and 14 each comprising an upper frame member 16, a lower frame member 18, a front frame member 20 and a rear frame member 22 forming the rectilinear configuration. The lower frame members 18 are interconnected by a transverse lower member 24 and the front frame members 20 are interconnected by a transverse front member 26. A generally rectangular leaf member 28 interconnects the rear frame members 22 and extends forwardly to a position proximate to the transverse front member 26. The transverse lower member 24, transverse front member 26 and the leaf member 28 secure the rectilinear frameworks 12 and 14 into their spaced-apart opposing relationship with each other.

The leaf member 28 comprises a generally rectangular configuration that in its relaxed state, extends generally parallel to the upper and lower frame members 16 and 18, but is allowed to pivot downwardly toward the transverse lower member 24 due to the fact that its leading front end is not connected to the front member 20 whereas its rearward most leading end is connected to the rear member 22 of the rectilinear frameworks 12 and 14.

The leaf clamp 10 of the invention further comprises a snap-lever 30 comprising a generally L-shaped configuration having opposing axles 32 which are rotatably journalled into corresponding axial holes 34 formed in the upper frames 16 of the rectilinear frameworks 12 and 14. More particularly, the snap-lever 30 comprises a longer leg portion 36 integrally formed with a shorter leg portion 38. Preferably, the angle between the longer and shorter leg portions 36 and 38 is greater than 90 degrees (i.e., obtuse) such that when the longer leg portion 36 is positioned generally parallel between the upper frames 16 of the frameworks 12 and 14, the shorter leg portion 38 extends beyond normal (i.e., beyond ninety degrees from a transverse line between the axis of the axles 32 and the transverse lower member 24).

During use, tubing whose flow is to be controlled by the leaf clamp 10, is positioned within a pathway under the leaf member between the opposing frameworks (i.e., threaded between the frameworks 12 and 14 and between the leaf member 28 and the transverse lower member 24). FIG. 2 shows the snap-lever 30 is in its transverse or "open" position. As best shown in FIG. 3, as the snap lever 30 is pivoted rearwardly from its transverse position of FIG. 2 to a parallel position of FIG. 3, the shorter leg portion 38 engages against the upper surface of the leaf member 28 to urge it downwardly into engagement with the tubing position therebelow. Further pivoting of the snap-lever 30 toward its parallel "closed" position further moves the shorter leg portion 38 to a position normal (i.e., ninety degrees) to the tubing. Still further movement of the longer leg portion 36 of the snap-lever 30 toward its parallel "closed" position, moves the shorter leg portion 38 beyond normal relative to the tubing whereupon the snap-lever 30 is snapped closed by the inherent resiliency of the tubing exerting a force against the now-non-perpendicular shorter leg portion 38. Consequently, it should be appreciated that a snapping action is readily observed and appreciated to assure that the leaf clamp 10 has indeed been snapped closed.

Conversely, moving the longer leg portion 36 of the snap-lever from its parallel "closed" position causes the shorter leg portion 38 to move from its non-normal, non-perpendicular position relative to the tubing, past it and then beyond whereupon a "snap-open" action is attained due to the inherent resiliency of the tubing exerting a force on the leaf member 20 to snap-open the snap-lever 30 to its generally transverse "open" position.

It should be appreciated that the leaf member 28 squeezes the tubing upon closure of the snap lever 30. Consequently, the friction and resulting wear that might otherwise be imparted to the tubing by the shorter leg portion 38 (without the leaf member 28) is eliminated. Still further, it should be appreciated that the particular type of synthetic resin used to manufacture the leaf clamp 10 may be chosen with increased inherent lubrication properties facilitating opening and closing of the leaf clamp with the shorter leg portion 38 of the snap-lever 30 gliding on the leaf member 28.

As shown in FIGS. 1-6, the snap-lever 30 may be injection molded as one component and the rectilinear frameworks 12 and 14 together with the transverse lower and front members 24 and 26 and the leaf member 28 may be injection-molded as another component, whereupon after injection, the axles 32 of the snap-lever 30 may be fitted into the axial holes 34 by hand or through the use of an assembly machine.

Alternatively, however, the leaf clamp 10 may be injection-molded as a multi-component fully-assembled device in accordance with my invention set forth in my patent applications entitled "Apparatus and Method for Injection Molding a Fully-Assembled Multi-Component Articulatable Device", Ser. No. 60/939,347, filed May 21, 2007 and Ser. No. 12/124,342, filed May 21, 2008, the disclosures of which are hereby incorporated by reference herein.

Figure 5:
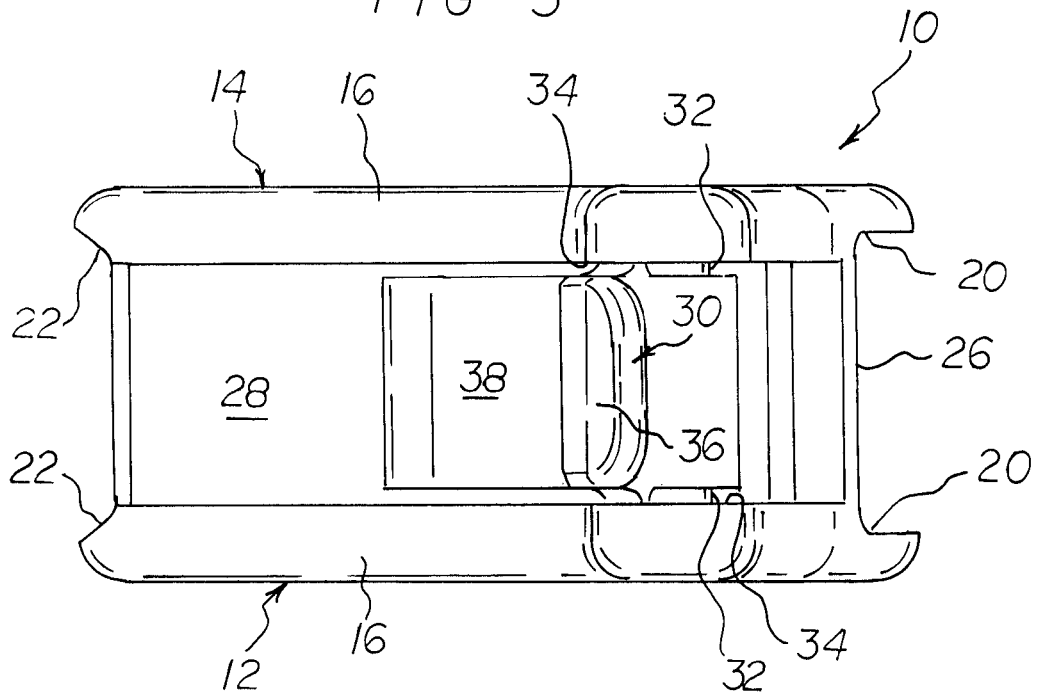
FIG. 5 is a top plan view of FIG. 1 showing the self-aligning feature of the snap-lever during closing as it is guided between the upper rails of the opposing rectilinear frameworks.
Figure 6:
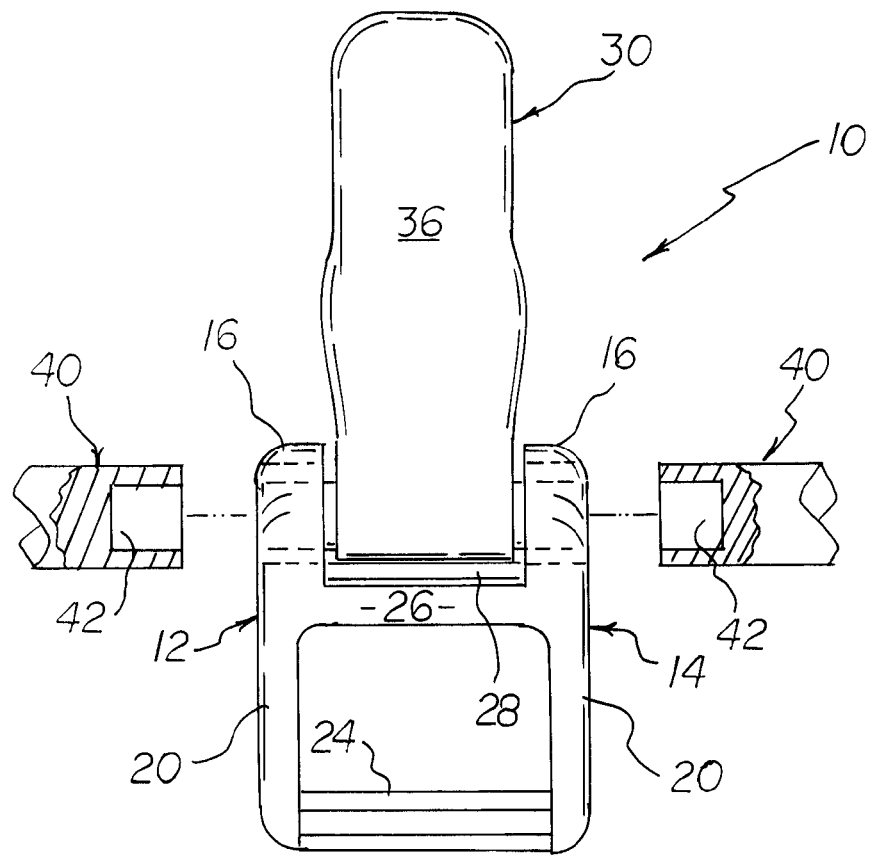
FIG. 6 is a front view of FIG. 1 showing the spacing between the snap-lever and the upper rails of the opposing rectilinear frameworks that allow the leaf clamp of the invention to be manufactured in accordance with my invention described in my patent application entitled "Apparatus and Method for Injection Molding a Fully-Assembled Multi-Component Articulatable Device", described in my patent application Ser. No. 60/939,347, filed May 21, 2007 and Ser. No. 12/124,342, filed May 21, 2008, the disclosures of which are hereby incorporated by reference herein.
Figure 7:
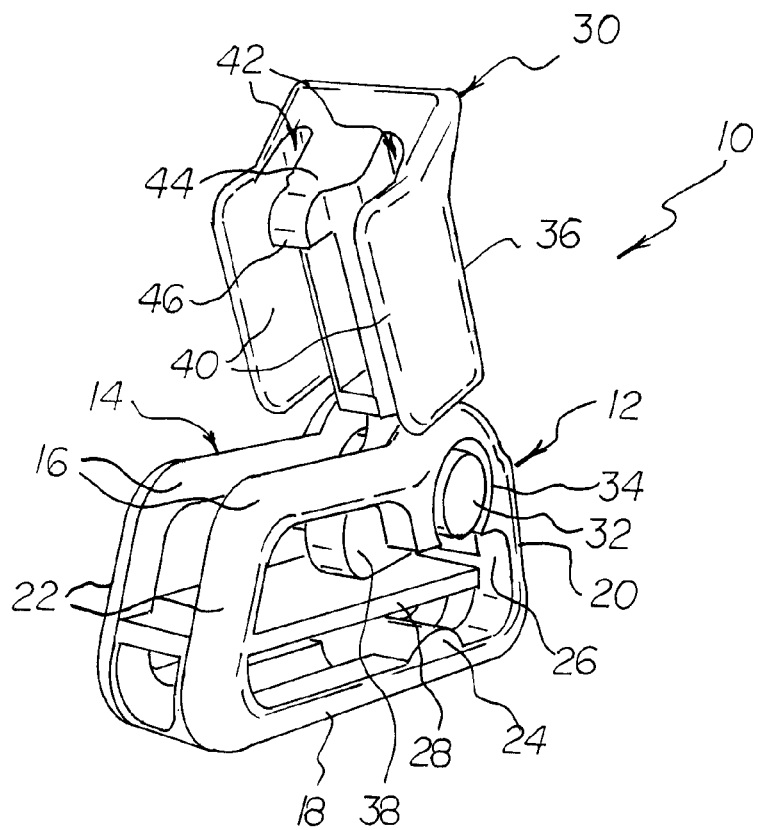
FIG. 7 is a top rearward perspective view of another embodiment of the leaf clamp of the invention wherein its snap lever comprises opposing shrouds that fit over the upper members of the framework to provide support thereto and to assure that the snap lever self-aligns itself during closure.
Figure 8:
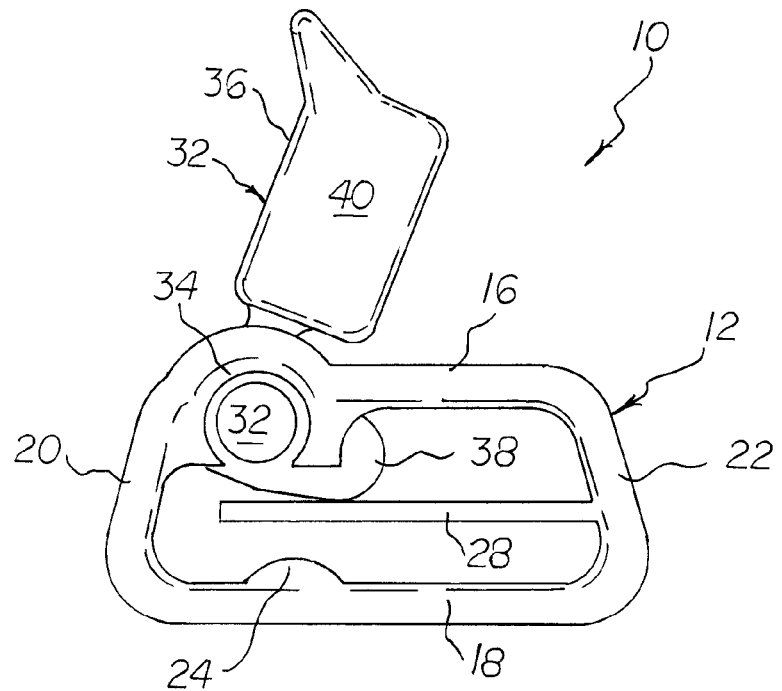
FIG. 8 is a right side view of FIG. 7.
Figure 9:
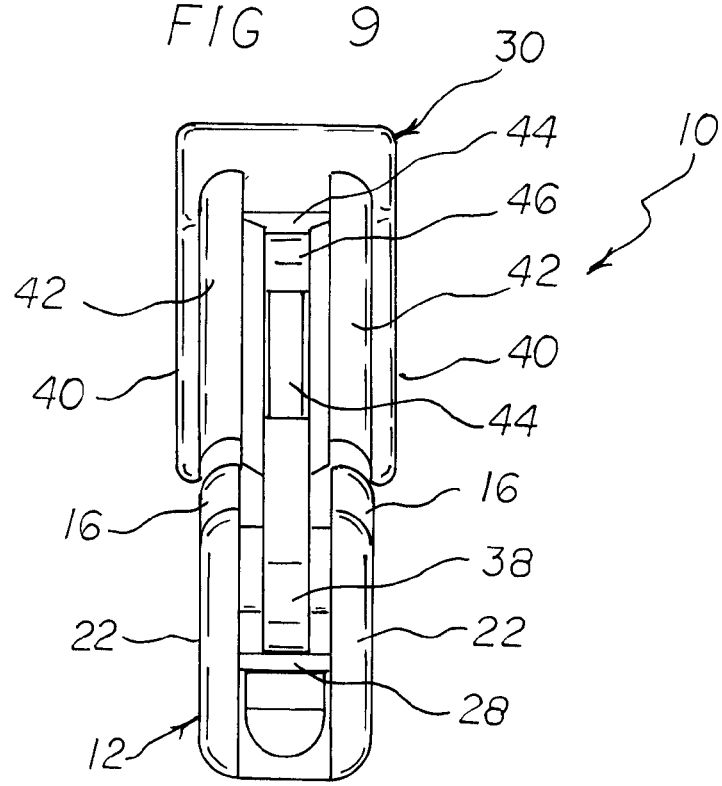
FIG. 9 is a rear view of FIG. 7.
Figure 10:
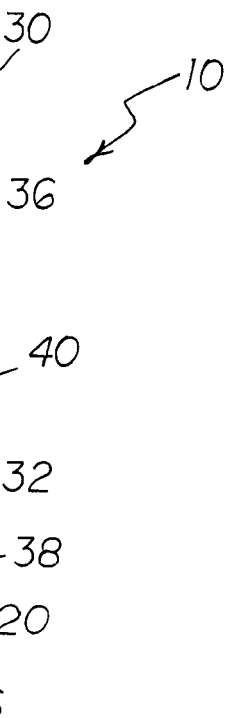
FIG. 10 is a front view of FIG. 7.

More particularly, as best shown in FIGS. 5 and 6, the snap-lever 30 may be loosely fitted between the rectilinear frameworks 12 and 14 to create a sufficient space therebetween such that, in accordance with my other invention, the snap-lever 30 and frameworks 12 and 14 may be injection-molded together in the mold. Specifically, as shown in phantom in FIG. 6, the axial holes 34 formed in the frameworks 12 and 14 and the axles 32 formed on the snap-lever 30 may be formed during injection of the snap-lever 30 and framework 12 and 14 components by the use of gated core pins 40 having a axial blind hole 42 formed in the ends thereof that define the axial hole 34 and the axles 32, respectively, during injection.

Referring to FIGS. 7-10, another embodiment of the leaf clamp 10 of the invention comprises a pair of opposing rectilinear frameworks 12 and 14 similar to those of the embodiment shown in FIGS. 1-6. Likewise, the embodiment of the leaf clamp of FIGS. 7-10 includes a leaf member 28 similar to that described in connection with the embodiments of FIGS. 1-6. Consequently, the reference numerals identifying similar features of the embodiment of FIGS. 1-6 are repeated in the embodiment shown in FIGS. 7-10.

In the embodiment of the leaf clamp 10 shown in FIGS. 7-10, its snap lever 30 comprises a generally L-shaped configuration having opposing axles 32 which are rotatably journalled into corresponding axial holes 34 formed in the upper frames 16 of the rectilinear frameworks 12 and 14. The snap lever 30 comprises a longer leg portion 36 integrally formed with a shorter leg portion 38. The snap lever 30 additionally comprises a pair of opposing alignment shrouds 40 extending downwardly from the opposing sides of the longer leg portion 36 of the snap lever 30. Spacing between the opposing alignment shrouds 40 comprises a close fit relative to the outer dimension of the opposing upper frames 16 of the frameworks 12 and 14. The alignment shrouds 40 function to provide lateral support to the upper frame 16 of the frameworks 12 and 14 to assure that they do not flex or bow laterally outwardly. Further, alignment shrouds 40 serve to self-align the longer leg portion 36 of the snap lever 30 relative to the frameworks 12 and 14 during closure of the snap lever 30. This self-alignment feature precludes any skewing of the snap lever 30 during closure as might otherwise occur due to the loose-fit of the opposing axles 32 that are rotatably journalled into the corresponding axial holes 34 formed in the upper frames 16 of the rectilinear frameworks 12 and 14.

The longer leg portion 36 of the snap lever 30 may additionally include opposing alignment slots 42 formed therein in parallel with the opposing alignment shrouds 40. The cross-sectional configurations of the alignment slots 42 are preferably the same as the cross-sectional configurations of the respective upper frames 16 of the frameworks 12 and 14, respectively. The alignment slots 42 provide additional support for the upper frames 16 once the snap lever 30 is moved to its fully horizontal, closed position.

In addition to the alignment shrouds 40 and the alignment slots 42, the snap lever 30 may additionally comprise an elongated central alignment boss 44 extending downwardly from the center of the other side of the snap lever 30. The longitudinal corners of the alignment boss 44 are angled (i.e., champhered) to facilitate longitudinal alignment of the longer leg portion 36 relative to the upper frame 16 of the frameworks 12 and 14 during closure of the snap lever 30. Additionally, the alignment boss 44 may include a stop member 46 extending downwardly from the rearward portion thereof to seat itself on top of the leaf member 28 when the snap lever 30 has been moved to its fully closed position.

As described in connection with the embodiment of FIGS. 1-6, the shrouded embodiment of the leaf clamp 10 shown in FIGS. 7-11 similarly functions to snap-close and snap-open during closure and opening of the clamp 10 due to the inherent resiliency of the tubing. More particularly, upon partial closing of the snap lever 30, its shorter leg portion 38 forces the leaf member 28 downwardly into engagement with the tubing. Further closure of the snap lever 30 causes its shorter leg portion 38 to fully compress the tubing once the shorter leg portion 38 is perpendicular thereto. Full closure of the snap lever 30 to its horizontal position, causes its shorter leg portion 38 to move slightly beyond a position perpendicular relative to the tubing such that the inherent resiliency of the compressed tubing "snaps" the leaf clamp 10 closed and holds it in a closed position due to the inherent resiliency of the tubing.

Upon opening of the leaf clamp 10 of the invention, initial upward movement snap lever 30 moves its shorter leg portion 38 to a position perpendicular to the tubing and then past it, whereupon the inherent resiliency of the tubing "snap-opens" the snap lever 30. Thus, it should be appreciated that a user is provided with a forceful tactile indication of the opening and closing of the leaf clamp 10. Further, the user is able to quickly visualize whether the leaf clamp 12 is opened or closed based upon whether the longer leg portion 36 of the snap lever 30 is positioned transversely or is horizontally disposed relative to the frameworks 12 and 14 (i.e., flush).

The frameworks 12 and 14 and the snap lever 30 may be injection molded as separate components and then subsequently assembled together by hand or by machine. However, the frameworks 12 and 14 and the snap lever 30 may alternatively be injection molded as a multi-component, fully-assembled articulatable device as described in connection with the embodiment of FIGS. 1-6. During multi-component injection molding, the leaf clamp 10 is injection molded in a multi-component mold with the snap lever 30 positioned fully forward in parallel alignment with the rectangular frameworks 12 and 14.

The present disclosure includes that contained in the appended claims, as well as that of the foregoing description. Although this invention has been described in its preferred form with a certain degree of particularity, it is understood that the present disclosure of the preferred form has been made only by way of example and that numerous changes in the details of construction and the combination and arrangement of parts may be resorted to without departing from the spirit and scope of the invention.

Now that the invention has been described,

What is claimed is:

1. A leaf clamp for clamping onto a tube to control the flow of a fluid therethrough, comprising in combination:
   opposing frameworks defining a pathway for receiving the tube;
   a leaf member interconnecting the opposing frameworks and extending above the pathway; and
   a generally L-shaped snap lever having a shorter leg and a longer leg, the snap lever being pivotally connected between upper portions of the opposing frameworks with the shorter leg aligned for engagement with the leaf member to urge the leaf member toward the pathway to squeeze the tube positioned in the pathway as the longer leg of the snap lever is pivoted from a generally transverse "open" position to a generally parallel "closed" position.

2. The leaf clamp as set forth in claim 1, wherein the angle between the shorter leg and the longer leg of the snap-lever is obtuse such that upon movement of the snap lever to the parallel "closed" position, the resilient force of the tube being squeezed by the leaf member snaps the snap lever closed and such that upon movement of the longer leg of the snap lever from the parallel "closed" position to the generally transverse "open" position causes the snap lever to snap open.

3. The leaf clamp as set forth in claim 1, wherein the snap lever and the opposing frameworks interconnected by the leaf member are injection molded as separate components and then subsequently assembled.

4. The leaf clamp as set forth in claim 1, wherein the snap lever and the opposing frameworks interconnected by the leaf member are simultaneously injected molded assembled.

5. The leaf clamp as set forth in claim 1, wherein the opposing frameworks each comprises upper frame member, a lower frame member, a front frame member and a rear frame member, with the lower frame members of the opposing frameworks being interconnected by a transverse lower member and the front frame members of the opposing frameworks being interconnected by a transverse front member.

6. The leaf clamp as set forth in claim 5, wherein the leaf member interconnects the rear frame members of the opposing frameworks and extends forwardly to a position proximate to the transverse front member.

7. The leaf clamp as set forth in claim 6, wherein the leaf member is composed of a resilient material and, in a relaxed state, extends generally parallel to the upper frame members and the lower frame members of the opposing frameworks.

8. The leaf clamp as set forth in claim 7, wherein a rearward end of the leaf member is connected to the front member such that a forward end of the leaf member may pivot downwardly toward the pathway by movement of the snap lever to the "closed" position.

9. The leaf clamp as set forth in claim 8, wherein the snap lever comprises opposing axles rotatably journalled into corresponding axial holes formed in the upper frames of the opposing frameworks.

10. The leaf clamp as set forth in claim 9, wherein an angle between the longer leg and the shorter leg of the snap lever is obtuse such that when the snap lever is positioned in the "closed" position, the longer leg is positioned generally parallel between the upper frames of the frameworks and the shorter leg extends beyond ninety degrees from a transverse line between the axis of the axles and the transverse lower member.

11. The leaf clamp as set forth in claim 9, wherein the snap lever comprises a pair of opposing alignment shrouds extending downwardly from opposing sides of the longer leg and being spaced apart to define a close fit relative to an outer dimension of the upper frames of the opposing frameworks, thereby self-aligning the longer leg of the snap lever relative to the frameworks during closing of the snap lever and providing lateral support to the upper frames of the opposing frameworks after closing of the snap lever.

12. The leaf clamp as set forth in claim 11, wherein the longer leg of the snap lever comprises opposing alignment slots extending parallel with the opposing alignment shrouds.

13. The leaf clamp as set forth in claim 12, wherein a cross-sectional configuration of the alignment slots are substantially the same as a cross-sectional configuration of the respective upper frames of the opposing frameworks to provide support for the upper frames once the snap lever is moved to the "closed" position.

14. The leaf clamp as set forth in claim 12, wherein the snap lever comprises an elongated central alignment boss extending downwardly.

15. The leaf clamp as set forth in claim 14, wherein longitudinal corners of the alignment boss are angled to facilitate longitudinal alignment of the longer leg relative to the upper frame of the frameworks during closure of the snap lever.

16. The leaf clamp as set forth in claim 15, wherein the alignment boss includes a stop member extending downwardly from a rearward portion thereof to seat on top of the leaf member when the snap lever has been moved to the "closed" position.

\* \* \* \* \*